US012403900B2

(12) United States Patent
Fan et al.

(10) Patent No.: US 12,403,900 B2
(45) Date of Patent: Sep. 2, 2025

(54) COLLISION-AVOIDANCE SYSTEM AND METHOD IN A MAGNETIZING ENVIRONMENT

(71) Applicant: Medcaptain Medical Technology Co., Ltd., Shenzhen (CN)

(72) Inventors: Jiajun Fan, Shenzhen (CN); Yuchen Wei, Shenzhen (CN); Yaoqi Zhong, Shenzhen (CN)

(73) Assignee: Medcaptain Medical Technology Co., Ltd., Shenzhen (CN)

( * ) Notice: Subject to any disclaimer, the term of this patent is extended or adjusted under 35 U.S.C. 154(b) by 213 days.

(21) Appl. No.: 18/336,114

(22) Filed: Jun. 16, 2023

(65) Prior Publication Data
US 2023/0331221 A1 Oct. 19, 2023

Related U.S. Application Data

(63) Continuation-in-part of application No. PCT/CN2020/137404, filed on Dec. 17, 2020.

(51) Int. Cl.
*B60W 30/095* (2012.01)
*B60W 50/14* (2020.01)

(52) U.S. Cl.
CPC ......... *B60W 30/095* (2013.01); *B60W 50/14* (2013.01); *B60W 2050/143* (2013.01); *B60W 2510/18* (2013.01)

(58) Field of Classification Search
None
See application file for complete search history.

(56) References Cited

U.S. PATENT DOCUMENTS 6,630,891 B1 * 10/2003 Dilling ................. G08G 1/0965
340/901
8,416,076 B2 * 4/2013 Mamourian ............. G08B 3/10
600/410

(Continued)

FOREIGN PATENT DOCUMENTS

| CN | 203029261 | 7/2013 |
| CN | 204106034 | 1/2015 |

(Continued)

OTHER PUBLICATIONS

Merged Foreign Copy and English Translation of CN 104133183 A (Year: 2014).*

(Continued)

*Primary Examiner* — James J Lee
*Assistant Examiner* — Andrew Sang Kim
(74) *Attorney, Agent, or Firm* — Jeffrey Pearce

(57) ABSTRACT

A device control system, method, electronic device, and storage medium are applied within a magnetizing environment such as a Magnetic Resonance environment. The device control system includes a magnetic field detecting module configured to determine a magnetic field intensity at the location of the first device; and/or, a distance determining module configured to determine a distance between the first device and the second device; a monitoring module configured to generate an alarm command according to the magnetic field intensity and/or the distance; and a control module configured to control the first device according to the alarm command.

17 Claims, 9 Drawing Sheets

(56) References Cited

U.S. PATENT DOCUMENTS

| | | | | |
|---|---|---|---|---|
| 2011/0121986 A1* | 5/2011 | Kopp | ................. | B82Y 25/00 |
| | | | | 340/657 |
| 2012/0112747 A1 | 5/2012 | Alexiuk et al. | | |
| 2018/0297506 A1* | 10/2018 | Stefan | ................. | G01S 15/08 |
| 2022/0308135 A1* | 9/2022 | Djajadiningrat | ..... | G01R 33/288 |

FOREIGN PATENT DOCUMENTS

| | | |
|---|---|---|
| CN | 108898815 | 11/2018 |
| CN | 210271137 | 4/2020 |
| CN | 210383915 | 4/2020 |
| EP | 3748383 A1 | 12/2020 |
| JP | 2005192857 | 7/2005 |
| JP | 2013063148 | 4/2013 |
| WO | 2011/062725 A3 | 5/2011 |
| WO | 2016/142747 A1 | 9/2016 |

OTHER PUBLICATIONS

Merged Foreign Copy and English Translation of CN 110733555 B (Year: 2020).*
Rosebrock, NPL—Measuring distance between objects in an image with OpenCV (Year: 2016).*

* cited by examiner ers a variety
COLLISION-AVOIDANCE SYSTEM AND METHOD IN A MAGNETIZING ENVIRONMENT

REFERENCE TO RELATED APPLICATIONS

The present application is a bypass continuation-in-part of International Application No. PCT/CN2020/137404, filed on Dec. 17, 2020, the entire contents of which are incorporated herein by reference.

TECHNICAL FIELD

The present disclosure generally relates to the field of device control technologies, and more particularly, to a device control system, method, electronic device, and storage medium for collision avoidance in a magnetizing environment.

BACKGROUND OF THE INVENTION

Magnetic Resonance Imaging (MRI) is a widely used medical imaging technique that utilizes the phenomenon of magnetic resonance to obtain electromagnetic signals from the human body and reconstruct information and tomographic images. The environment in which MRI is performed is referred to as the Magnetic Resonance (MR) environment. While MRI offers advantages such as a variety of imaging modalities and rich information, its strong magnetic field characteristic also brings certain inconveniences. For instance, there is a risk of magnetization of metallic enclosures in the MR environment.

In the case of devices that need to be frequently moved within the MR environment, such as ventilators, they are typically placed on carts with wheels for ease of mobility. However, in the MR environment, the magnetized metallic enclosures of these devices can generate magnetic attraction these devices and other devices, objects, and surfaces within the MR environment. This can lead to unintended movement of the cart and ultimately result in collisions. These collisions can cause significant damage and financial losses, especially for costly MRI devices such as imaging machines.

SUMMARY OF THE INVENTION

In order to solve the above-mentioned problems in the related art, embodiments of the present application provide a device control apparatus, method, electronic device, and storage medium applied to the magnetizing environment, which can stop the movement of the device before the device collision and prevent the damage caused by the device collision.

According to a first aspect, embodiments of the present application provide a device control system applied to a magnetizing environment, for example a Magnetic Resonance (MR) environment, comprising:
   a magnetic field detecting module configured to determine a magnetic field intensity at a location of the first device; and/or, a distance detecting module configured to determine a distance between the first device and a second device;
   a monitoring module configured to generate an alarm command according to the magnetic field intensity and/or the distance; and
   a control module configured to control the first device according to the alarm command.

According to a second aspect, embodiments of the present application provide a device control method applied to a Magnetic Resonance (MR) environment, comprising:
   determining a magnetic field intensity at a location of the first device; and/or, determining a distance between the first device and a second device;
   generating an alarm command according to the magnetic field intensity and/or the distance; and
   controlling the first device according to the alarm command. Note that the first and second aspects do not need to be exclusive but can be included in the same system.

According to a third aspect, embodiments of the present application provide an electronic device, comprising a processor, a memory, a communication interface, and one or more programs; wherein the one or more programs are stored in the memory and are configured to be executed by the processor, the one or more programs comprising instructions for performing the steps in the method of:
   determining a magnetic field intensity at a location of the first device; and/or, determining a distance between the first device and a second device;
   generating an alarm command according to the magnetic field intensity and/or the distance; and
   controlling the first device according to the alarm command.

According to a fourth aspect, embodiments of the present application provide a computer-readable storage medium, wherein the computer-readable storage medium stores a computer program, the computer program being executed by a processor to implement a method comprising:
   determining a magnetic field intensity at a location of the first device; and/or, determining a distance between the first device and a second device;
   generating an alarm command according to the magnetic field intensity and/or the distance; and
   controlling the first device according to the alarm command.

According to a fifth aspect, embodiments of the present application provide a computer program product, comprising a non-transitory computer-readable storage medium on which a computer program is stored, the computer program being operable to cause the computer to perform a method comprising:
   determining a magnetic field intensity at a location of the first device; and/or, determining a distance between the first device and a second device;
   generating an alarm command according to the magnetic field intensity and/or the distance; and
   controlling the first device according to the alarm command.

The embodiments of the present application to be implemented may have the following beneficial effects.

As can be seen, in the embodiments of the present application, the magnetic field intensity of the location of the first device is determined by the magnetic field detecting module, and the distance between the first device and the second device is determined by the distance detecting module, and then the risk of the first device being attracted to the second device is determined according to the magnetic field intensity and distance, so that the first device is controlled before the attraction occurs, thereby avoiding collisions between devices, improving the safety of the devices in the MR environment, and preventing losses due to device collisions.

BRIEF DESCRIPTION OF THE DRAWINGS

In order to illustrate the technical solutions in the embodiments of the present application more clearly, the accompanying drawings to be used in the description of the embodiments will be briefly described below. Obviously, the accompanying drawings in the following description are some embodiments of the present application; for a person having ordinary skill in the art, other accompanying drawings can be obtained without creative work.

DETAILED DESCRIPTION

The technical solutions in the embodiments of the present application will be described clearly and completely as follows in conjunction with the accompanying drawings in the embodiments of the present application, and it is clear that the embodiments described are a part of rather than all of the embodiments of the present application. Based on the embodiments in the present application, all other embodiments obtained by a person having ordinary skill in the art without creative labor fall within the protection scope of the present application.

The terms "first", "second", "third", and "fourth" in the specification and claims of the present application and the accompanying drawings described herein are used to distinguish between different objects but not used to describe a particular order. In addition, the terms "include" and "have", and any variations thereof, are intended to cover non-exclusive inclusion. For example, a process, method, system, product, or device that includes a series of steps or units is not limited to the listed steps or units, but optionally also includes steps or units that are not listed, or optionally also includes other steps or units that are inherent to the process, method, system, product, or device.

References herein to "embodiment" mean that particular features, results, or characteristics described in conjunction with an embodiment may be included in at least one embodiment of the present application. The presence of this item at various points in the specification does not necessarily mean the same embodiment, nor is it a separate or alternative embodiment that is mutually exclusive with other embodiments. It is understood, both explicitly and implicitly, by the person having ordinary skill in the art that the embodiments described herein may be combined with other embodiments.

Figure 1:
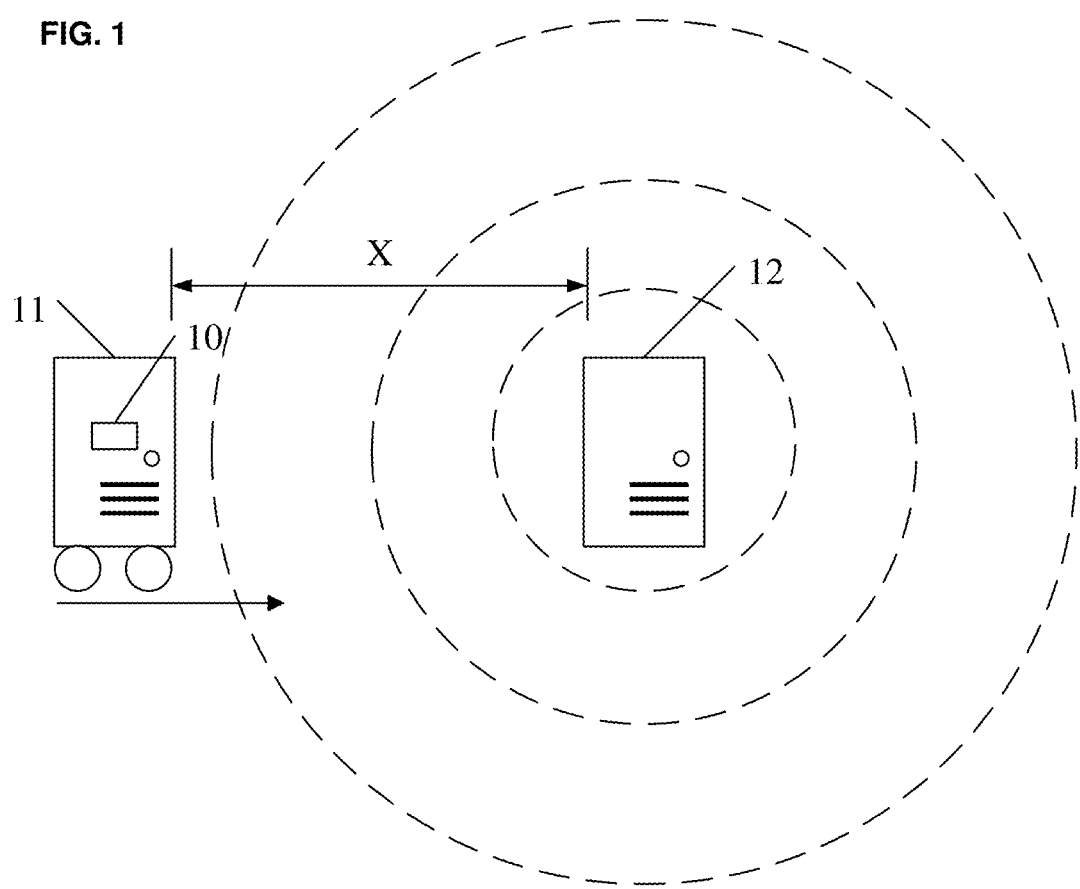
FIG. 1 shows an application scenario of a device control system used in a magnetizing environment according to an embodiment of the present application.

Refer to FIG. 1, which shows an application scenario of a device control system used within a magnetizing environment. Since a common magnetizing environment is a Magnetic Resonance (MR) environment, embodiments of the invention are described below primarily with reference to such an MR environment. Magnetizing environments may also arise in other contexts, however, and need not be "permanent" in the sense of objects that have been externally magnetized by, for example, an MRI machine. In some environments, devices may create strong electro-magnetic fields, such as when large electric motors, solenoids, etc., are activated. The invention may be used in such environments as well; any needed modifications of embodiments described below will be apparent to most engineers.

The first device 11 is a movable device with wheels, tracks, slides, etc., and the control system 10 is provided in the first device. The second device 12 is a device also located in the MR environment. A distance between the first device 11 and the second device 12 is indicated as X, and there is a magnetic field (illustrated as concentric circles) extending outward and decreasing around the second device 12. In many situations, the second device will be stationary, either permanently or temporarily, but this is not a requirement for the invention. It may also be the case that the second device is also movable—the invention prevents collisions, which in practice means that the distance X is reduced to 0 (or to whatever distance involves collision). Moreover, the term "device" in the context of this invention is intended to be interpreted broadly to include any type of object, surface, etc., in particular with reference to the second device. The second device could, for example, be a magnetized surface, metal table, that could generate a strong enough magnetic field to cause the first device to move. In other words, neither the first nor the second "device" must necessarily be a "machine".

In this embodiment, the control system 10 includes or communicates with a collision risk estimation module, which can determine a magnetic field intensity at a location of the first device 11 and/or a distance between the first device 11 and the second device 12. The collision risk estimation module associated with the control system 10 further determines a risk level of mutual attraction based on the magnetic field intensity and/or the distance. If the risk level is too high, the control system 10 generates an alarm command, to control the first device 10 to enter a braked state, thereby preventing great damage due to the collision of the first device with the second device.

Figure 2:
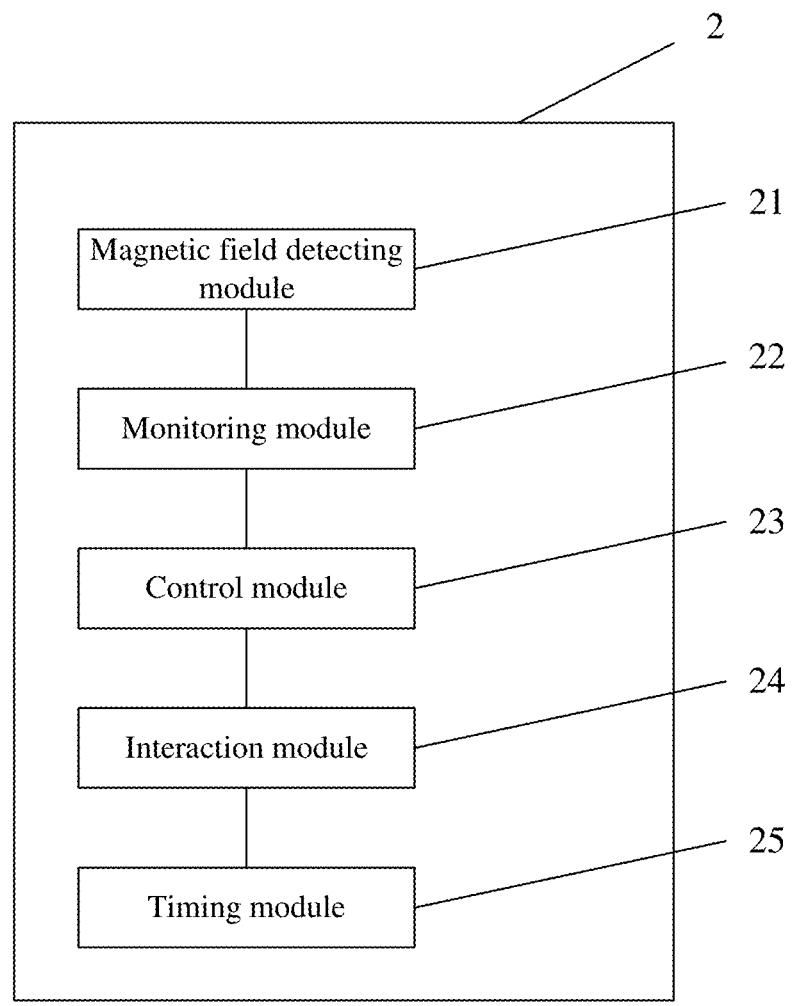
FIG. 2 is a block diagram of a functional module of the device control system applied to the magnetizing environment according to an embodiment of the present application.

Refer to FIG. 2, which is a block diagram of a functional module of the device control system applied to the MR environment according to an embodiment of the present application. The device control system 2, used within the MR environment is provided in the first device, and the control system 2 includes a magnetic field detecting module 21, a monitoring module 22, and a control module 23, each of which is described separately below.

(1) The magnetic field detecting module 21 is configured to determine the magnetic field intensity at a location of the first device and thus operates as, or comprises at least one component of, the collision risk estimation module.

Due to the fixed positioning of the second device within the MR environment, the surrounding magnetic field intensity is also constant. Therefore, the distance relationship between the first device and the second device can be determined by obtaining the magnetic field intensity at the location of the first device. Generally speaking, a Gauss meter may be used as the magnetic field detecting module 21. The Gauss meter has the advantages of wide measurement range, real-time measurement capability and high sensitivity in magnetic field measurement. However, the Gauss meter is tested in a point test manner, which has the defects of inaccurate measurement, different values measured by different manufacturers of Gauss meter, and different values measured by different probes of the same Gauss meter.

Therefore, in embodiments in which magnetic field strength is used to determine proximity between the first and second devices, the present application provides a magnetic field detecting module 21. As one example, the magnetic field detecting module 21 may include a closed container, a light intensity detecting module, a light emitting module, and a processing module. The closed container is filled with a magnetorheological fluid, and the magnetorheological fluid is mixed with non-ferrous metal particles. The light emitting module is provided at a bottom end of the closed container and is configured to emit a light beam to irradiate the light intensity detecting module. The light intensity detecting module is provided at a top end of the closed container and is configured to detect a light intensity of the light beam irradiated by the light emitting module and send the light intensity to the processing module. The processing module is configured to receive the light intensity and determine the magnetic field intensity according to the light intensity.

Specifically, the magnetorheological fluid (MR fluid) is a new fluid with controlled fluidity. It exhibits low viscosity Newtonian fluid properties in the absence of an external magnetic field, and appears as a Bingham fluid with high viscosity and low flowability when a magnetic field is applied. There is a corresponding relationship between the viscosity of the fluid and the magnetic flux. Moreover, the magnetorheological fluid with such viscosity and flowability has advantages of low energy consumption, it's easy to control, and it has fast response (milliseconds).

Figure 3:
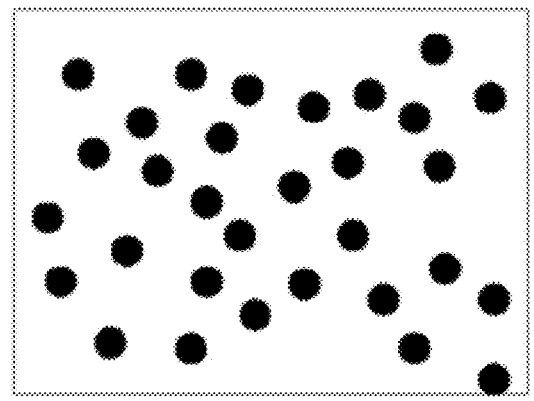
FIGS. 3a-3c show a distribution of non-ferrous metal particles in a magnetorheological fluid at different magnetic field intensities.
Figure 3:
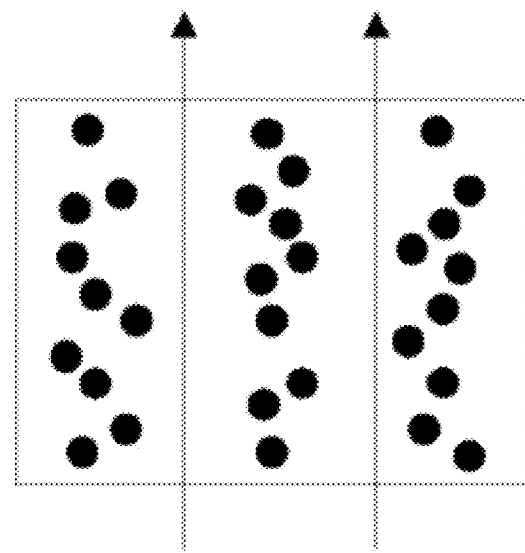
Figure 3:
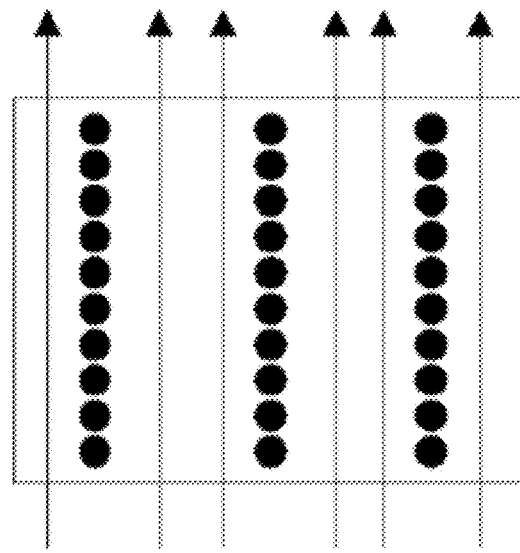

Under this liquid characteristic, as shown in FIG. 3(*a*), the nonferrous metal particles in the magnetorheological liquid show an irregular and disordered distribution in the absence of magnetic field, and this disordered distribution leads to a low light transmittance of the magnetorheological liquid. In contrast, when the magnetic field is applied, as shown in FIGS. 3(*b*) and 3(*c*), the nonferrous metal particles form a chain-like distribution with the direction of the magnetic field, and the stronger the magnetic field is, the more regularly the chains form. Gaps are then also form between the chains, leading to a larger light transmittance of the magnetorheological fluid. Therefore, the magnetic field intensity of the environment can be accurately determined based on the difference in the transmittance of the magnetorheological fluid with non-ferrous metal particles at different magnetic field intensities.

In addition, in the embodiment, the light emitted by the light emitting module may be a high frequency and highly penetrating violet light. The non-ferrous metal particles may be iron particles with lower cost and good magnetic properties. In an embodiment, the diameter of iron particles is 1.2-1.6 um, so that the detection accuracy of the magnetic field detecting module 21 can be further improved, and the costs are reduced.

In addition, an embodiment of the present application further provides another more commonly used method of detecting magnetic field intensity by a Hall effect sensor and other circuit components. In this embodiment, the magnetic detecting module includes a Hall sensor and a processor. The Hall sensor is provided in the first device and is configured to generate a Hall voltage. The processor is configured to receive the Hall voltage and determine the magnetic field intensity according to the Hall voltage. When a constant current is applied to the Hall sensor, it induces a Hall voltage in the magnetic field, and the level of the Hall voltage is proportional to the magnetic field intensity where the Hall device is located. Overall, magnetic field measurements with Hall sensors offer the advantages of non-contact, fast response, high sensitivity, wide measurement range, low power consumption and small size.

In an embodiment, the control system 2 may include at least two magnetic field detecting modules 21, thereby preventing the system from being paralyzed in case one of them fails. Additionally, the presence of multiple magnetic field detecting modules 21 allows for comparing their respective measurement results, thereby improving the measurement accuracy and optimizing the control of the first device by the control system 2.

(2) The monitoring module 22 is configured to generate an alarm command according to the magnetic field intensity.

In this embodiment, a multi-level alarm command is used to achieve a multi-level control of the first device. For example, when the magnetic field intensity is greater than a first threshold value, the alarm command is a first alarm command, which raises an alarm to remind the user to transfer the first device away from its current position. This is because there is a risk of attraction to the device in this environment, but the risk level is relatively low. In other words, there is a possibility of being attracted, but the possibility is so low as to be negligible. Therefore, there is no need to control the first device, but only to issue an alarm to remind the user to transfer the first device away from its current position.

When the magnetic field intensity is greater than a third threshold value, the alarm command is a second alarm command, in which the third threshold value is greater than the first threshold value. The second alarm command is configured to issue the alarm and control the first device to enter a braked state. This is because there is a risk of attraction to the device in this environment, and the risk level is high. In other words, the possibility is high enough that the attraction between the first and second devices is great enough to lead to a collision, and emergency braking means are required to prevent the devices from colliding. Therefore, in addition to issuing an alarm, it is necessary to control the first device to enter a braked state.

In an embodiment, the present application further provides a client for receiving alarm commands issued by the monitoring module 22. The client may include a smartphone (such as an Android phone, an iPhone Operating System (iOS) phone, a Windows Phone), a tablet computer, a palmtop computer, a laptop computer, a Mobile Internet Device (MID), and other electronic devices that can receive information. When the client is a small movable electronic device such as a smartphone, it can be carried by the user at any time so that the user can be informed in a timely manner through the client when an alarm occurs, and thus send feedback commands to the control system 2 through the client to pre-process the alarm.

In an embodiment, the present application further provides a server, which is configured to receive the alarm command issued by the control system 2, receive the feedback commands sent by the client, and store the alarm command and feedback commands for easy analysis and recall later.

(3) The control module 23 is configured to control the first device according to the alarm command.

In this embodiment, the control module 23 may include an alarm module and a brake module, to control the first device in conjunction with the multi-level alarm generated by the monitoring module 22.

For example, when the alarm command received by the control module 23 is the first alarm command, only the alarm module is called for alarming to remind the user to transfer the first device away from the current position. When the alarm command received by the control module 23 is the second alarm command, both the alarm module and the brake module are called. Specifically, the alarm is performed by the alarm module to remind the user to transfer the first device away from the current position, and at the same time, the brake is performed by the brake module to put the first device into the braked state so as to prevent the first device from colliding with the second device before the user operates it.

Refer to FIG. 2, which shows that, in this embodiment, the device control system 2 further includes an interaction module 24 and a timing module 25. The interaction module 24 is configured to receive a release command issued by the user when the first device is in the braked state and send the release command to the brake module. The brake module is configured to release the braked state of the first device after receiving the release command, so that the user can transfer the first device away from its current position.

In this embodiment, the timing module 25 is configured to start timing after the braked state of the first device is released. During a delay period of T seconds, the magnetic field detecting module control system refrains from issuing alarm signals, but after the delay period has expired again determines a current magnetic field intensity at the location of the first device. If the current magnetic field intensity is greater than the first threshold value, a lock command is generated and the lock command is sent to the brake module. In this case, it means that the user does not transfer the first device away from the dangerous position after issuing the release command. Temporary halting of the issuance of alarm signals may similarly be implemented in the embodiments in which collision risk is based on direct distance measurement instead of magnetic field intensity. Therefore, in order to prevent a collision, the timing module 25 issues a lock command to cause the brake module to perform a locking process to lock the wheels of the first device, thereby achieving a secondary protection for the device. This may also be desirable in situations in which the user actually wants or needs the first device to be located close to the second device: By releasing the brake the user would have T seconds in which to position the first device, after which its brakes will be automatically applied if the user hasn't already done so manually. It would also be possible to implement an "override" function in the interaction module 24 such that the user can command brake release for the first device regardless of its location relative to the second device. This could be programmed to last for some maximum time per command, after which the brakes are activated again, either by the control system or the user himself.

In addition, in this embodiment, the device control system 2 further includes an electromagnetic shielding module. The electromagnetic shielding module wraps the brake module to shield the influence of electromagnetic field on the brake module, thereby enhancing the reliability of the control system 2.

In summary, the device control system applied to the MR environment provided by the present application determines the magnetic field intensity at the location of the first device through the magnetic field detecting module, and then determines the collision risk of the first device caused by being attracted to the second device according to the magnetic field intensity, so as to control the first device before too great an attraction occurs, thereby avoiding the collision between devices and enhancing the safety of the devices in the MR environment. Besides, the multi-level alarm command is used to achieve a multi-level control of the first device, thus making the control process more accurate and convenient. In addition, after the user issues a release command, the first device location is further determined by the timing module to ensure that the user transfers the first device away from the dangerous position, and the wheels of the first device are locked if the user does not transfer the first device away from the dangerous position, thereby achieving a secondary protection of the device.

Figure 4A:
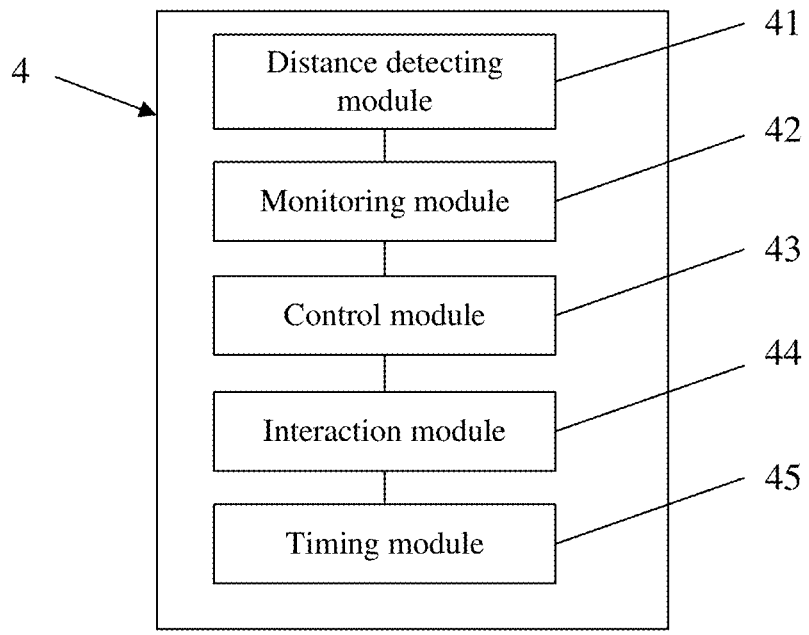
FIG. 4A is a block diagram of a functional module of another device control system applied to the magnetizing environment according to an embodiment of the present application.
Figure 4B:
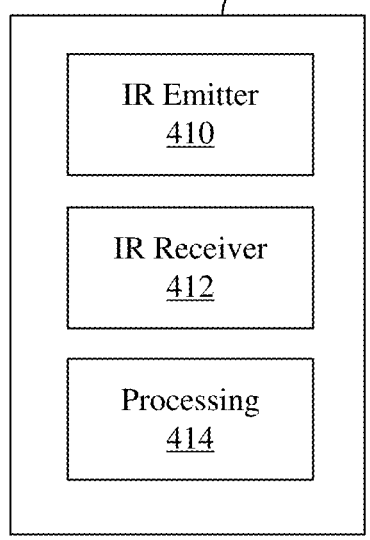
FIG. 4B illustrates an infrared-based embodiment of a distance detection module.
Figure 4C:
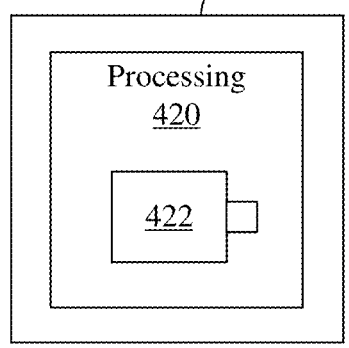
FIG. 4C illustrates embodiment of a distance detection module that uses optical imaging.

Refer to FIG. 4, which is a block diagram of a functional module of a different embodiment of the device control system 4 used within the magnetizing environment according to another embodiment of the present application. The device control system 4 in this embodiment is provided in the first device, and the control system 4 includes a distance detecting module 41, a monitoring module 42, a control module 43, an interaction module 44 and a timing module 45. In this embodiment, the distance detecting module 41 comprises or is one component (for example, along which the module to measure magnetic field intensity) of the collision risk estimation module. The specific implementation process of the monitoring module 42, control module 43, interaction module 44 and timing module 45 is similar to that of the monitoring module 22, control module 23, interaction module 24 and timing module 25 of control system 2 in FIG. 2, and will not be repeated here.

The distance detecting module 41 will now be described.

In this embodiment, the distance detecting module 41 is configured to determine a distance between the first device and the second device.

In this embodiment, since the magnetic field intensity around the second device is a given, the risk level of the first device being attracted to the second device can be determined according to the distance between the first device and the second device.

Since the MR environment is a special environment in a strong magnetic field, any distance measurement method based on electromagnetic correlation will be affected to a certain extent, leading to a decrease in distance measurement accuracy and affecting the control accuracy and efficiency of the control system.

Therefore, in this embodiment, the distance detecting module 41 (see FIG. 4B) may include an infrared emitting module 410, an infrared receiving module 412, and a processing module 414. The infrared emitting module is provided at a position on the first device facing the second device and is configured to transmit an infrared light to the second device. The infrared receiving module is configured to receive the infrared light reflected by the second device. The processing module is configured to determine a distance between the first device and the second device according to an emission time of the infrared emitting module emitting the infrared light to the second device and a reception time of the infrared receiving module receiving the infrared light reflected by the second device. The distance between the two devices is determined by determining the time from the emission to the time of reflection of infrared light. This method has the advantages of fast positioning, simple operation, high accuracy, and it is not easily affected by strong magnetic fields.

In another embodiment (see FIG. 4C), the processing module 420 in the distance detecting module 41 is configured to:

establish a three-dimensional coordinate space and mark the second device as an origin of this space; obtain at least one image containing the first device from at least one camera module 422 and determine at least one pixel coordinate of the first device in the at least one image; determine a spatial coordinate of the first device in the three-dimensional space according to the at least one pixel coordinate and the at least one camera module, and determine a distance between the spatial coordinate and the origin as the distance between the first device and the second device.

For example, the three-dimensional space may be obtained by pre-scanning the real space where the MR environment is located by a simultaneous localization and mapping device. After generating the three-dimensional space, the second device is set as the origin, and the camera module set in the MR environment is mapped to the corresponding position in the three-dimensional space.

As a result, after obtaining the at least one image containing the first device, the camera modules that took the image feed back their shooting angle information, and the pixel coordinate of the first device in each image is obtained through image processing. Thus, by combining the shooting angle information and pixel coordinates returned by multiple camera modules, a corresponding scene can be constructed in the three-dimensional space, and the spatial coordinates of the first device in the three-dimensional space can be determined. This method can accurately determine the location of the first device with almost negligible error, which can greatly improve the control accuracy and efficiency of the control system.

In addition, in this embodiment, the multi-level alarm command is also configured to achieve the multi-level control of the first device. For example, when the distance between the first device and the second device is less than the second threshold, the alarm command generated by the monitoring module 42 is the first alarm command, and the first alarm command is configured to raise an alarm to remind the user to transfer the first device away from its current position. This is because there is a risk of attraction to the device at this distance, but the risk level is relatively low. In other words, there is a possibility of being attracted, but the possibility is so low as to be negligible. Therefore, there is no need to control the first device, but only to issue an alarm to remind the user to transfer the first device away from its current position.

When the distance between the first device and the second device is less than the fourth threshold, the alarm command generated by the monitoring module 42 is a second alarm command, in which the fourth threshold is less than the second threshold. The second alarm command is configured to issue the alarm and control the first device to enter the braked state. This is because there is a risk of attraction to the device at this distance, and the risk level is high. In other words, the possibility of being attracted leading to a collision is high, and emergency braking means are required to prevent the device from colliding. Therefore, in addition to issuing an alarm, it is necessary to control the first device to enter a braked state.

In addition, in this embodiment, the device control system 4 further includes an electromagnetic shielding module. The electromagnetic shielding module wraps around the distance detecting module 41 and the brake module to shield the influence of electromagnetic field on the distance detecting module 41 and the brake module, thereby enhancing the reliability of the control system 2.

In summary, in this embodiment, applying the device control system to the MR environment, the distance between the first device and the second device is determined by the distance detecting module, and then the risk of the first device being attracted to the second device is determined according to the distance between the first device and the second device, so as to control the first device before the force of attraction becomes too great and thereby avoiding the collision between the devices and enhancing the safety of the device in the MR environment. Besides, the multi-level alarm command is used to achieve the multi-level control of the first device, thereby making the control process more accurate and convenient.

Figure 5:
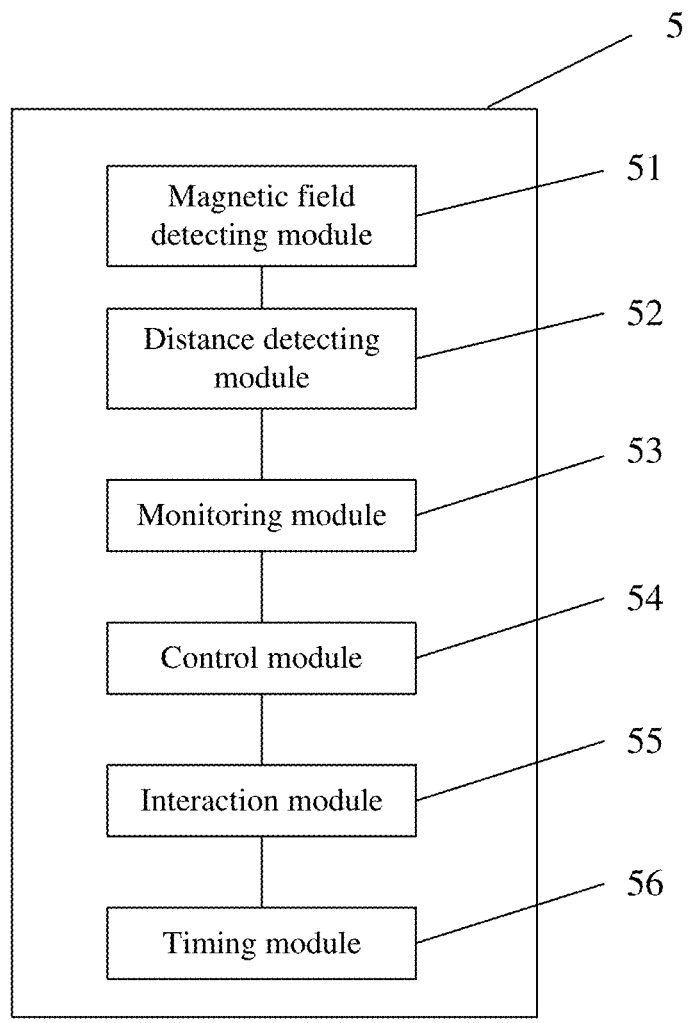
FIG. 5 is a block diagram of a functional module of another device control system applied to the magnetizing environment according to an embodiment of the present application.

Refer to FIG. 5, which is a block diagram of a functional module of another device control system applied to the MR environment according to an embodiment of the present application. The device control system 5 applied to the MR environment is provided in the first device, and the control system 5 includes a magnetic field detecting module 51, a distance detecting module 52, a monitoring module 53, a control module 54, an interaction module 55, and a timing module 56.

The specific implementation process of the magnetic field detecting module 51, the monitoring module 53, the control module 54, the interaction module 55 and the timing module 56 is similar to the specific implementation process of the magnetic field detecting module 21, the monitoring module 22, the control module 23, the interaction module 24 and the timing module 25 of the control system 2 in FIG. 2, and will not be repeated here.

The specific implementation process of the distance detecting module 52 is similar to the specific implementation process of the distance detecting module 41 of the control system 2 in FIG. 4, and will not be repeated here.

In addition, in this embodiment, the device control system 5 further includes an electromagnetic shielding module. The electromagnetic shielding module wraps around the distance detecting module 52 and the brake module to shield the influence of electromagnetic field on the distance detecting module 52 and the brake module, thereby enhancing the reliability of the control system 2.

In summary, in the device control system applied to the MR environment provided by the present application, the magnetic field intensity at the location of the first device is determined by the magnetic field detecting module, the distance between the first device and the second device is determined by the distance detecting module, and then the risk of the first device being too strongly attracted to the second device is determined according to the magnetic field intensity and the distance between the first device and the second device, forming a double insurance. Therefore, the first device is controlled before the force of attraction becomes too great, thereby avoiding collisions between devices and enhancing the safety of the device in the MR environment.

Figure 6:
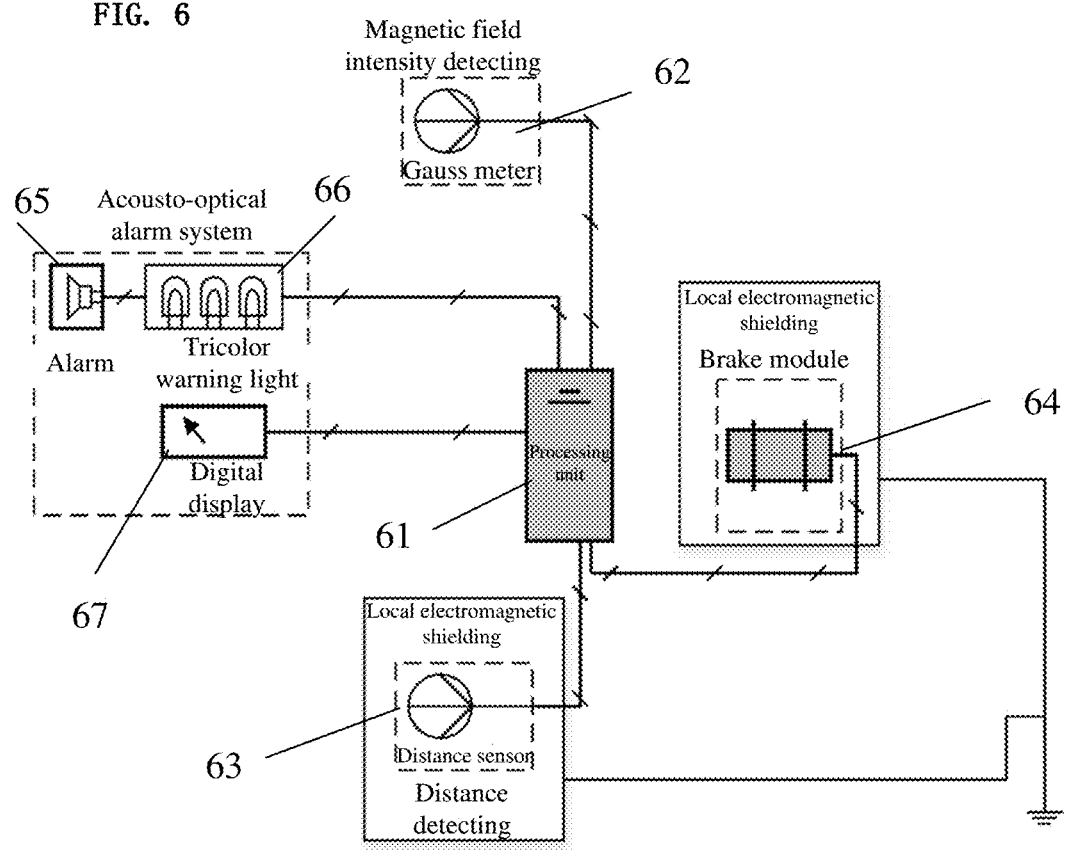
FIG. 6 is a structural diagram of a device control apparatus applied to the magnetizing environment according to an embodiment of the present application.

Refer to FIG. 6, which is a structural diagram of a device control apparatus applied to the MR environment according to an embodiment of the present application. The device control apparatus applied to the MR environment is provided in the first device, and the control device includes a processing unit 61, a Gauss meter 62, a distance sensor 63, a brake module 64, an alarm 65, a tricolor warning light 66, and a digital display 67.

The processing unit 61 is connected to the Gauss meter 62, the distance sensor 63, the brake module 64, the tricolor warning light 66, and the digital display 67, respectively. The alarm 65 is connected to the processing unit 61 through the tricolor warning light 66. The alarm 65, tricolor warning light 66 and digital display 67 form an acousto-optical alarm module, and an area where the brake module 64 and the distance sensor 63 are located is an electromagnetic shielded area.

Figure 7:
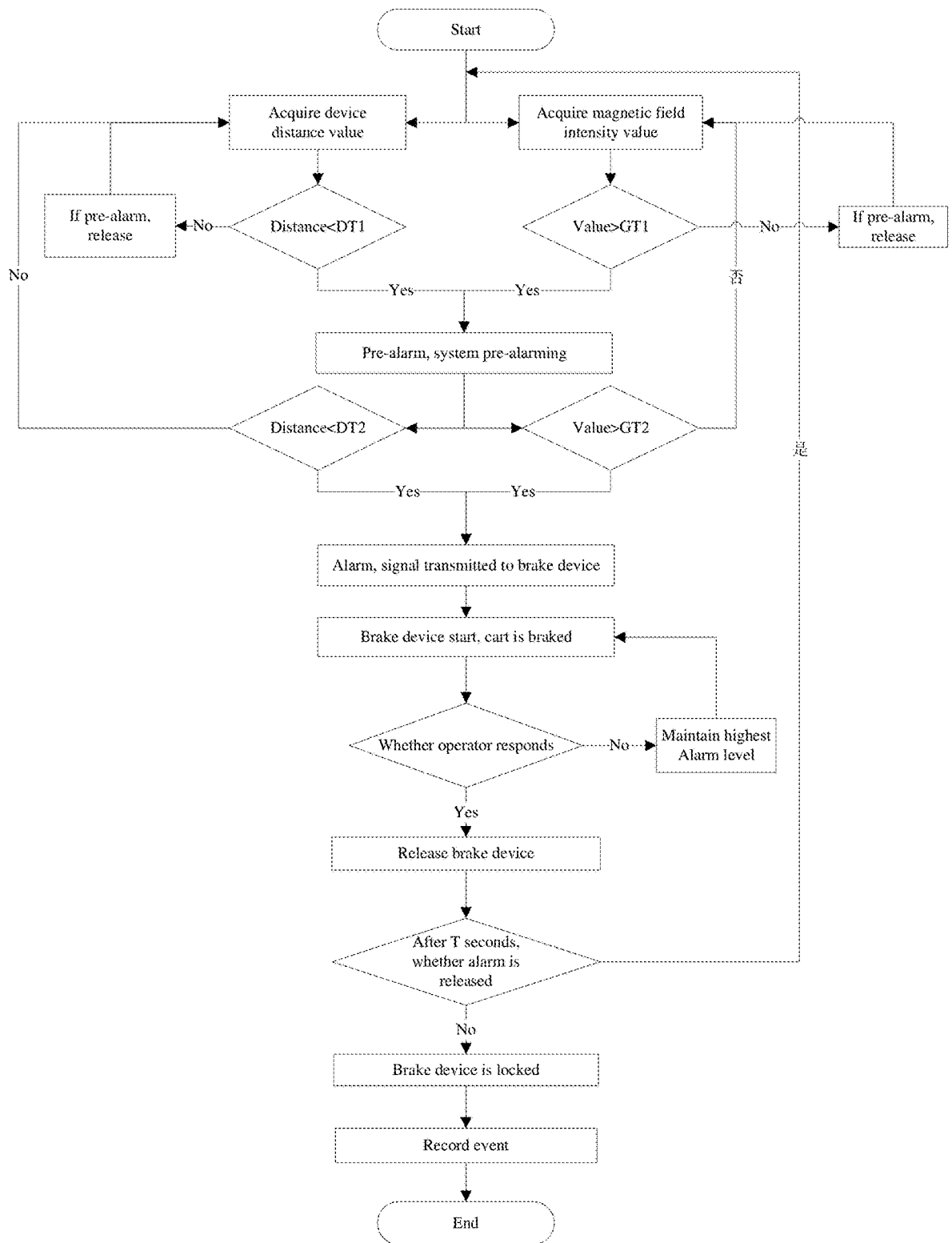
FIG. 7 is an operational flowchart of the device control apparatus applied to the magnetizing environment according to an embodiment of the present application.

For example, as shown in FIG. 7, the control unit 6 operates as follows:

When the control device 6 is started, the distance sensor 63 starts working for real-time distance detecting. When the acquired distance value is greater than DT1 (the warning distance value DT1, when the device is in this position, there is only a small risk of being too strongly magnetically attracted, and no emergency braking means is required), the control device does not take any action and the distance sensor 63 continues to work. When the acquired distance value is less than DT1, a pre-alarming signal is issued through the acousto-optical alarm module to remind the operator to transfer the device and avoid collision.

While issuing the pre-alarming signal by the acousto-optical alarm module, the distance value is further determined. If the distance value is less than DT2 (dangerous distance value DT2, when the device is in this position, there is a risk of being attracted too strongly, and the risk level is high, so that the emergency braking means need to be taken to prevent device collision), the brake module 64 is activated to brake the first device. If the distance value is greater than DT2, the brake module 64 will not be activated.

At the same time, the Gauss meter 62 also starts to detect the magnetic field intensity in real time. When the acquired Gauss meter value is less than GT1 (warning magnetic field intensity value GT1, when the device is in this kind of environment, there is magnetic attraction, but the risk level that the force of attraction is low and no emergency braking means is required), the control device does not take any action, and the Gauss meter 62 continues to work. When the acquired Gauss meter value is greater than GT1, a warning alarm signal is issued by through the acousto-optical alarm module to remind the operator to transfer the device and avoid collision.

While issuing the pre-alarming signal through the acousto-optical alarm module, the magnetic field intensity value is further determined. If the magnetic field intensity value is greater than GT2 (dangerous magnetic field intensity value GT2, when the device is in this position, there is a high risk of being too strongly magnetically attracted, so that emergency braking means are required to prevent device collision), the brake module 64 is started to brake the first device. If the magnetic field intensity value is less than GT2, the brake module 64 will not start.

When the brake module 64 starts, the signal is transmitted to a signal receiver at the brake device. After receiving the signal, the braking device is immediately activated to stop the cart and prevent further collision close to the second device.

The operator can temporarily release the brake device through the digital display 67 and move the device away from the dangerous position. After disengagement, the control device is reset.

If the operator does not move the device away from the dangerous position within T seconds after releasing the braking device, the brake device will again issue a hold command to protect the device a second time.

Figure 8:
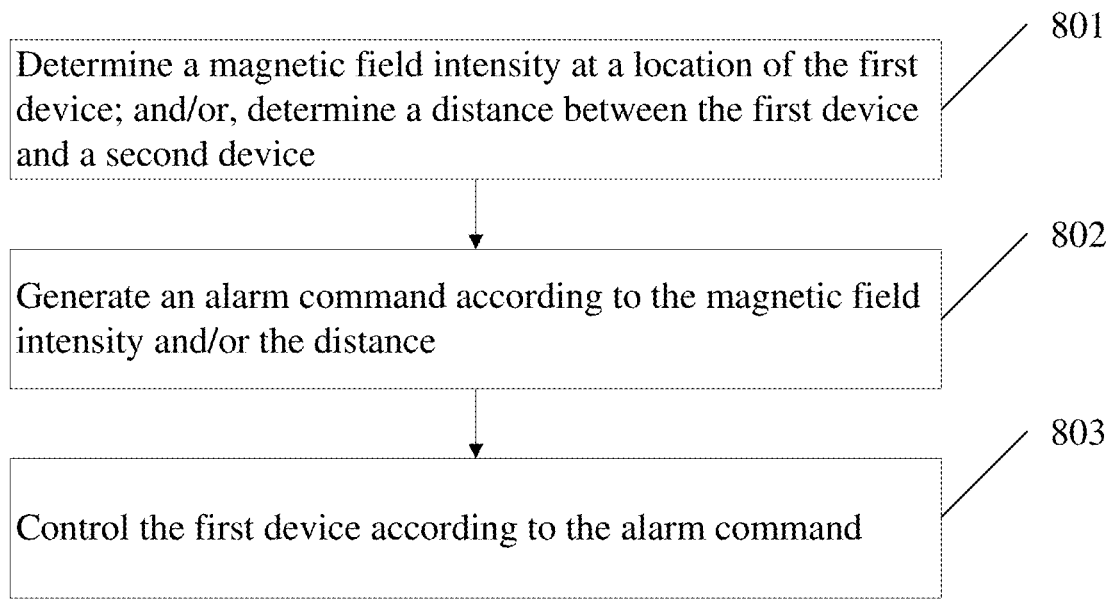
FIG. 8 is a flowchart of a device control method applied to the magnetizing environment according to an embodiment of the present application.

Refer to FIG. 8, which is a flowchart of a device control method applied to the MR environment according to an embodiment of the present application. As shown in FIG. 8, the device control method applied to the MR environment includes the following steps.

801: a magnetic field intensity at a location of the first device is determined; and/or, a distance between the first device and a second device is determined.

802: an alarm command is generated according to the magnetic field intensity and/or the distance.

803: the first device is controlled according to the alarm command.

It should be understood that the specific implementation process of the various steps of the method shown in FIG. 8 can be found in the specific implementation process of the various modules in the system described in any of FIG. 2, FIG. 4 and FIG. 5 above, and will not be repeated here.

Figure 9:
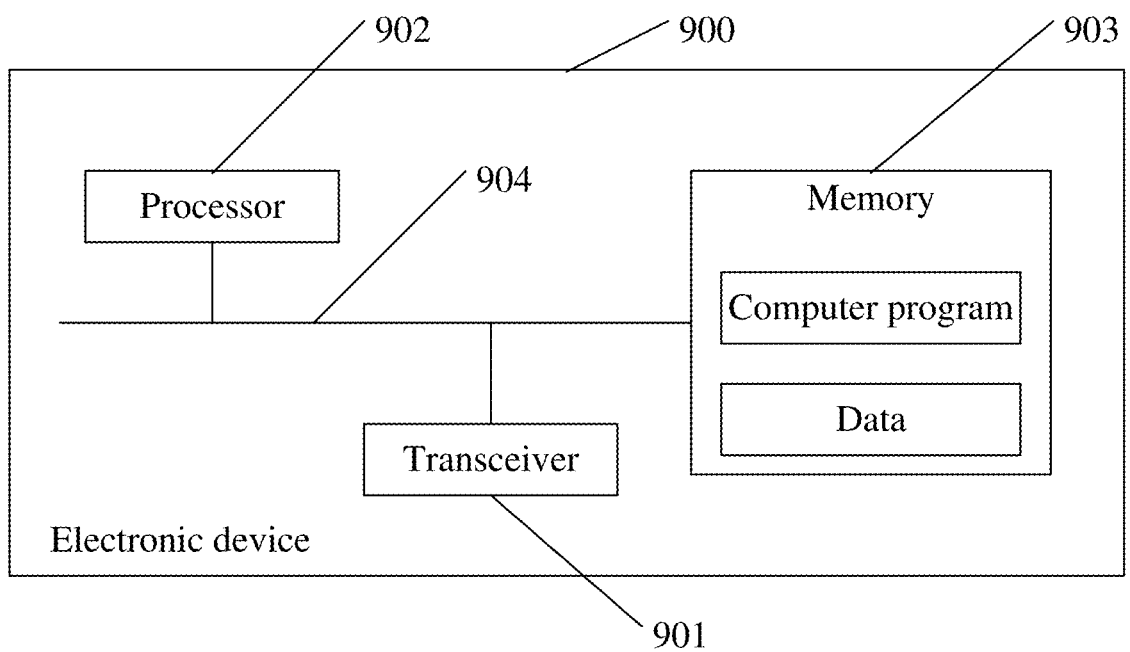
FIG. 9 is a structural diagram of an electronic device according to an embodiment of the present application.

Refer to FIG. 9, which is a structural diagram of an electronic device according to an embodiment of the present application. As shown in FIG. 9, the electronic device 900 includes a transceiver 901, a processor 902, and a memory 903, which are connected to each other through a bus 904. The memory 903 is configured to store computer programs and data and can transfer the data stored in the memory 903 to the processor 902.

The processor 902 is configured to read the computer program in the memory 903 to perform the following operations.

A magnetic field intensity at a location of the first device is determined; and/or, a distance between the first device and a second device is determined.

An alarm command is generated by the collision risk estimation module according to the magnetic field intensity and/or the distance.

The first device is controlled according to the alarm command. It should be understood that the specific implementation process of the individual operations performed by the processor 902 shown in FIG. 9 can be found in the specific implementation process of the individual modules in the system described in any of FIG. 2, FIG. 4 and FIG. 5 above, and will not be repeated herein.

It should be understood that the device control apparatus applied to the MR environment in the present application may be a smartphone (e.g., Android phone, iOS phone, Windows Phone), a tablet computer, a handheld computer, a laptop computer, a mobile Internet device (MID), a robot or a wearable device, etc. The above-mentioned device control apparatus applied to the MR environment are only examples, not an exhaustive list, which is not limited to the above-mentioned device control apparatus applied to the MR environment. In practical applications, the above-mentioned device control apparatus applied to MR environment may also be an intelligent vehicle terminal or a computer device.

Through the description of the above embodiments, it is clear to the person having ordinary skill in the art that the present application can be realized with the combination of software and a hardware platform. Based on this understanding, all or part of the technical solution of the present application that contributes to the background technologies may be embodied in the form of a software product, which may be stored in a storage medium, such as ROM/RAM, disk, CD-ROM, including a number of instructions to enable a computer device (which may be a personal computer, a server, or a network device, etc.) to execute the method described in each embodiment or some part of the embodiments of the present application.

Accordingly, the present application embodiment further provides a computer-readable storage medium. The computer-readable storage medium stores a computer program, and the computer program is executed by a processor to implement some or all of the steps of the device control method applied to the MR environment as described in the above-method embodiments. For example, the storage medium may be a hard disk, a floppy disk, an optical disk, a magnetic tape, a diskette, a thumb drive, a flash memory, etc.

Embodiments of the present application further provide a computer program product, including a non-transitory computer-readable storage medium storing a computer program, the computer program being operable to cause the computer to perform some or all of the steps of the device control method applied to the MR environment as described in the above-method embodiments.

It should be noted that each of the above-mentioned method embodiments is presented as a series of combinations of actions for simplicity of description, but it should be known to the person having ordinary skill in the art that the present application is not limited by the sequence of actions described, as certain steps may be performed in other sequences or simultaneously according to the present application. Secondly, the person having ordinary skill in the art should also be aware that the embodiments described in the specification are optional and the actions and modules involved are not necessarily necessary for the present application.

In the above embodiments, the description of each embodiment has its own focus, and what is not described in detail in a particular embodiment may be found in the relevant descriptions of other embodiments.

In several of the embodiments provided in the present application, it should be understood that the disclosed apparatuses may be implemented in other ways. For example, the above described embodiments of the device are only schematic. The division of the units described, is only a logical functional division, and the practical embodiment may be divided in another way. Multiple units or components may be combined or integrated into another system, or some features may be ignored or not implemented. On another point, the mutual coupling or direct coupling or communication connections shown or discussed may be indirect coupling or communication connections through some interface, device or unit, either electrically or in other forms.

The units illustrated as separate components may or may not be physically separated, and the components shown as units may or may not be physical units, i.e., may be located in one place or may also be distributed to a plurality of network units. Some or all of these units may be selected according to practical needs to achieve the purpose of the scheme of the embodiments.

Additionally, each functional unit in each embodiment of the present application may be integrated in a processing unit, or each unit may be physically present separately, or two or more units may be integrated in a single unit. The integrated units may be implemented either in the form of hardware or in the form of software program modules.

The integrated unit, when implemented in the form of a software program module and sold or used as a separate product, may be stored in a computer-readable memory. It is understood that the technical solution of the present application, or that part or all or part of the technical solution which essentially contributes to the prior art, may be embodied in the form of a software product. The software product is stored in a memory and includes a number of instructions to enable a computer device (which may be a personal computer, server or network device, etc.) to perform all or part of the steps of the method described in the various embodiments of the present application. The above-mentioned memory may be USB flash drive, Read-Only Memory (ROM), Random Access Memory (RAM), removable hard disk, diskette, or CD-ROM, and various other media that can store program code.

The person having ordinary skill in the art can understand that all or some of the steps in the various methods of the above embodiments may be accomplished by instructing the relevant hardware through a program, which may be stored in a computer-readable memory. The memory may be a flash drive, Read-Only Memory (ROM), Random Access Memory (RAM), disk or CD-ROM, etc.

The above is a detailed description of the embodiments of the present application, and this paper applies specific examples to illustrate the principle and embodiments of the present application. The above description is only for the purpose of helping to understand the method of the present application and its core idea. In addition, for the person having ordinary skill in the art, according to the idea of the present application, there will be changes in the specific embodiments and the scope of application. In summary, the content of this description should not be understood as a limitation of the present application.

We claim:

1. A collision-avoidance system for devices located in a magnetizing environment, comprising:
 a first device, which comprises a control system, which in turn comprises a collision risk estimation module;
 said collision risk estimation module being provided to estimate a likelihood of collision between the first device and a second device due to a force of magnetic attraction;
 a monitoring module configured to generate at least one alarm command in response to a determination by the collision risk estimation module that the likelihood of collision exceeds at least one threshold value;
 a control module configured to control the first device according to the alarm command;
 a brake module via which the control module causes the first device to be braked in response to the alarm command;
 an interaction module configured to receive a release command issued by a user and send the release command to the brake module when the first device is in a braked state,
 said brake module being further configured to release the braked state of the first device according to the release command;
 a timing module configured to start a timing of a delay period after release of the braked state of the first device;
 in which the collision risk estimation module is configured to refrain from issuing the alarm command during the delay period and to direct the control module to automatically return the first device to the braked state at the end of the delay period in response to sensing by the collision risk estimation module that a current magnetic field intensity is greater than a first threshold value, indicating that the first device is in a position of being attracted to the second device at the end of the delay period.

2. The system of claim 1, in which the alarm command indicates a first-level risk condition and signals a user to relocate the first device and a second-level risk condition in which the control module causes the first device to be braked.

3. The system of claim 2, in which:
the collision risk estimation module comprises a magnetic field detecting module provided for measuring a magnetic field intensity of the second device at the first device; and
the alarm command is a first alarm command corresponding to the first-level risk condition when the magnetic field intensity is greater than the first threshold and is a second alarm command corresponding to the second-level risk condition when the magnetic field intensity is greater than a third threshold, said first threshold being less than said third threshold.

4. The system of claim 3, wherein the magnetic field detecting module, comprises:
a closed container;
a light intensity detecting module;
a light emitting module; and
a processing module;
wherein the closed container is filled with a magnetorheological fluid, the magnetorheological fluid being mixed with non-ferrous metal particles;
the light emitting module is provided at a bottom end of the closed container and is configured to emit a light beam to irradiate the light intensity detecting module;
the light intensity detecting module is provided at a top end of the closed container and is configured to detect a light intensity of the light beam irradiated by the light emitting module and send the light intensity to the processing module; and
the processing module is configured to receive the light intensity and determine the magnetic field intensity according to the light intensity.

5. The system of claim 3, wherein the magnetic field detecting module comprises:
a Hall sensor provided in the first device, and configured to generate a Hall voltage; and
a processor configured to receive the Hall voltage and determine the magnetic field intensity according to the Hall voltage.

6. The system of claim 2, in which:
the collision risk estimation module comprises a distance detecting module that determines a current distance between the first device and the second devices; and
the alarm command is a first alarm command corresponding to the first-level risk condition when the current distance is less than a second threshold and is a second alarm command corresponding to the second-level risk condition when the current distance is less than a fourth threshold, said fourth threshold being less than said second threshold.

7. The system of claim 6, further comprising:
an electromagnetic shielding module configured to wrap the distance detecting module and the brake module to shield the distance detecting module and the brake module from an influence of electromagnetic fields.

8. The system of claim 6, wherein the distance detecting module comprises:
an infrared emitting module;
an infrared receiving module; and
a processing module;
wherein the infrared emitting module is provided facing the second device and is configured to transmit an infrared light to the second device;
the infrared receiving module is configured to receive the infrared light reflected by the second device;
the processing module is configured to determine the distance between the first device and the second device according to an emission time of the infrared emitting module emitting the infrared light to the second device and a reception time of the infrared receiving module receiving the infrared light reflected from the second device.

9. The system of claim 6, wherein the distance detecting module comprises:
a processing module configured to:
establish a three-dimensional space, the three-dimensional space being generated by scanning a real space by a simultaneous localization and mapping device;
mark the second device as an origin of the three-dimensional space;
acquire at least one image from at least one camera module, wherein the at least one camera module is provided in an environment where the first device is located, and the at least one camera module corresponds to the at least one image one by one;
determine at least one pixel coordinate of the first device in the at least one image;
determine a spatial coordinate of the first device in the three-dimensional space according to the at least one pixel coordinate and the at least one camera module; and take a distance between the spatial coordinate and the origin as the distance between the first device and the second device.

10. The system of claim 1, in which the magnetizing environment is a Magnetic Resonance (MR) environment.

11. A method for collision-avoidance for devices located in a Magnetic Resonance (MR) environment, comprising:
estimating a likelihood of collision between a first device and a second device due to a force of magnetic attraction;
generating at least one alarm command in response to a determination that the likelihood of collision exceeds at least one threshold value; and
controlling the first device according to the alarm command via a brake module, braking the first device in response to the alarm command;
in an interaction module, generating a brake release command in response to user input and sending the release command to the brake module when the first device is in a braked state, said brake module being further configured to release the first device from the braked state according to the release command;
timing a delay period after release of the first device from the braked state;
refraining from issuing the alarm command during the delay period and automatically returning the first device to the braked state at the end of the delay period in response to sensing that a current magnetic field intensity is greater than a first threshold value, indicating that the first device is in a position of being attracted to the second device at the end of the delay period.

12. The method of claim 11, further comprising:
determining a first-level risk condition and a second-level risk condition;
signaling a user to relocate the first device in the first-level risk condition; and
causing the first device to be braked in the second-level risk condition.

13. The method of claim 12, further comprising:
estimating the likelihood of collision risk by measuring a magnetic field intensity of the second device at the first device; and
generating the at least one alarm command as a first alarm command corresponding to the first-level risk condition when the magnetic field intensity is greater than the first threshold and as a second alarm command corresponding to the second-level risk condition when the magnetic field intensity is greater than a third threshold, said first threshold being less than said third threshold.

14. The method of claim 12, further comprising:
estimating the likelihood of collision risk by determining a current distance between the first device and the second devices; and
generating the at least one alarm command as a first alarm command corresponding to the first-level risk condition when the current distance is less than a second threshold and as a second alarm command corresponding to the second-level risk condition when the current distance is less than a fourth threshold, said fourth threshold being less than said second threshold.

15. An electronic device, comprising:
a processor;
a memory;
a communication interface;
a brake module; and
one or more programs;
wherein the one or more programs are stored in the memory and are configured to be executed by the processor, the one or more programs comprising instructions for performing the steps of:
estimating a likelihood of collision between a first device and a second device due to a force of magnetic attraction within a magnetic resonance (MR) environment;
generating at least one alarm command in response to a determination that the likelihood of collision exceeds at least one threshold value;
controlling the first device according to the alarm command via the brake module, braking the first device in response to the alarm command; and
receiving a release command issued by a user and sending the release command to the brake module when the first device is in a braked state, thereby causing the brake module to release the braked state of the first device;
timing a delay period after release of the braked state of the first device;
after release of the braked state of the first device, refraining from issuing the alarm command during the delay period,
at the end of the delay period, when sensing that a current magnetic field intensity is greater than a first threshold, which indicates that the first device is in a position of being attracted to the second device, automatically returning the first device to the braked state.

16. The device of claim 15, in which the one or more programs further comprise instructions for performing the steps of:
estimating the likelihood of collision risk by measuring a magnetic field intensity of the second device at the first device; and
generating the at least one alarm command as a first alarm command corresponding to the first-level risk condition when the magnetic field intensity is greater than the first threshold and as a second alarm command corresponding to the second-level risk condition when the magnetic field intensity is greater than a third threshold, said first threshold being less than said third threshold.

17. The device of claim 15, in which the one or more programs further comprise instructions for performing the steps of:
estimating the likelihood of collision risk by determining a current distance between the first device and the second devices; and
generating the at least one alarm command as a first alarm command corresponding to the first-level risk condition when the current distance is less than a second threshold and as a second alarm command corresponding to the second-level risk condition when the current distance is less than a fourth threshold, said fourth threshold being less than said second threshold.

* * * * *